United States Patent [19]

Villa et al.

[11] Patent Number: 5,580,993
[45] Date of Patent: Dec. 3, 1996

[54] PROCESS FOR THE PREPARATION OF IOPAMIDOL AND 5-AMINO-2,2-DIALKYL-1,3-DIOXANES

[75] Inventors: Marco Villa, Milan; Antonio Nardi, Cusano Milanino, both of Italy

[73] Assignee: Zambon Group S.p.A., Vicenza, Italy

[21] Appl. No.: 304,178

[22] Filed: Sep. 12, 1994

[30] Foreign Application Priority Data

Sep. 10, 1993 [IT] Italy .................. MI93A1938

[51] Int. Cl.$^6$ .................. C07D 319/06; C07D 233/67
[52] U.S. Cl. .................. 549/371; 549/372; 564/153; 564/155; 564/158
[58] Field of Search .................. 549/371, 372; 564/153, 155, 158

[56] References Cited

U.S. PATENT DOCUMENTS 4,978,793  12/1990  Quirk et al. .

FOREIGN PATENT DOCUMENTS 550003   6/1974   Switzerland .
1472050  4/1977   United Kingdom .

*Primary Examiner*—Ba K. Trinh
*Attorney, Agent, or Firm*—Oblon, Spivak, McClelland, Maier & Neustadt, P.C.

[57] ABSTRACT

A process for the preparation of Iopamidol and 5-amino-2,2-dialkyl-1,3-dioxanes of formula

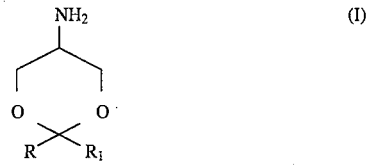

(I)

wherein R and $R_1$ are the same or different and represent a straight or branched $C_1$ and $C_2$ alkyl group or together with the carbon atom to which they are bonded, form a $C_5$–$C_6$ cycloaliphatic ring; comprising the transformation of a 2,2-dialkyl-1,3-dioxane-5-carboxylic acid ester of formula

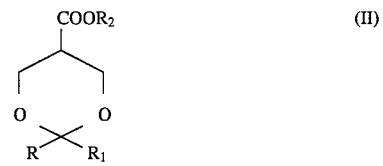

(II)

wherein $R_2$ represents a straight or branched $C_1$–$C_2$ alkyl group, a phenyl optionally substituted by nitro groups or a benzyl; by treatment with ammonia into the corresponding amides and the subsequent rearrangement of the latter into the compounds of formula I, by treatment with a hypohalogenite. The resultant ketals may be used as is, or be converted to 2-amino-1,3-propanediol, and reacted with 5-amino-2,4,6-triiodo-isophthalic acid dichloride or, alternatively, L-5-(2-acetoxy-propionylamino)-2,4,6-triido-isophthalic acid dichloride, to produce Iopamidol.

14 Claims, No Drawings

PROCESS FOR THE PREPARATION OF IOPAMIDOL AND 5-AMINO-2,2-DIALKYL-1,3-DIOXANES

BACKGROUND OF THE INVENTION

The present invention relates to a process for the preparation of Iopamidol and ketals of 2-amino-1,3-propanediol. More particularly the invention relates to a process for the preparation of 5-amino-2,2-dialkyl-1,3-dioxanes and use of the dioxanes to prepare Iopamidol.

The ketals of 2-amino-1,3-propanediol are advantageously used as synthetic intermediates in the preparation of the compound (S)-N,N'-bis-(2-hydroxy-1-(hydroxymethyl)ethyl]-5-[(2-hydroxy-1-oxopropyl)amino]-2,4,6-triido-1,3-benzenedicarboxamide, known with the International Nonproprietary Name of Iopamidol (Merck Index, XI ed., page 799, No. 4943).

Iopamidol was first described by the Swiss Company Savac A.G. in the British patent No. 1,472,050 and is used in diagnostics as a non ionic X-rays contrast medium. The preparation of Iopamidol, as described in said patent, comprises the condensation reaction of L-5-(2-acetoxy-propionylamino)-2,4,6-triido-isophthalic acid dichloride with 2-amino-1,3-propanediol, better known as serinol, in dimethylacetamide and in the presence of a base.

In the same patent, there is described an alternative method comprising the condensation reaction of the above acid dichloride, with a ketal of serinol. The subsequent acid hydrolysis of the formed diketal, carried out by conventional techniques, permits formation of the desired Iopamidol product. 5-Amino-2,2-dialkyl-1,3-dioxanes are among the possible ketals of serinol which can be used in the aforementioned synthesis of Iopamidol.

Several processes for the preparation of 5-amino-2,2-dialkyl-1,3-dioxanes are reported in the literature.

British patent application No. 2,081,256 (Rhône-Poulenc Industries) and U.S. Pat. No. 3,812,186 (Eprova A.G.) describe the preparation of 5-amino-2,2-dialkyl-1,3-dioxanes by catalytic hydrogenation of the corresponding 5-nitro derivatives, prepared, in turn, by direct cyclization of 2-nitro-1,3-propanediol with a suitable ketone, in the presence of boron trifluoride etheate.

U.S. Pat. No. 4,978,793 (W.R. Grace & Co.) describes the preparation of 5-amino-2,2-dialkyl-1,3-dioxanes. The process described involves synthesis of the corresponding 5-nitro-derivatives, through a three step process starting from nitromethane and formaldehyde, and subsequent reduction of the nitro group. The aforesaid processes for the preparation of 5-amino-2,2-dialkyl-1,3-dioxanes as described in the literature have the drawback of using nitro derivatives as intermediates, which are particularly unstable and explosive compounds.

One object of the present invention is a process for the preparation of 5-amino-2,2-dialkyl-1,3-dioxanes of the formula:

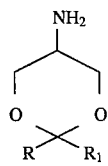

(I)

wherein R and $R_1$, are the same or different, and represent a straight or branched $C_1$–$C_3$ alkyl group or, together with the carbon atom to which they are bonded, form a $C_5$–$C_6$ cycloaliphatic ring.

A second object of the invention is the formation of 5-amino-2,2-dialkyl-1,3-dioxane of the formula I and the further reaction of the 5-amino-2,2-dialkyl-1,3-dioxane with 1-5-(2-acetoxy-propionylamino)-2,4,6-triido-isophthalic acid dichloride followed by hydrolysis to produce Iopamidol.

The 5-amino-2,2-dialkyl-1,3-dioxanes of formula I are prepared by a process comprising the transformation of a 2,2-dialkyl-1,3-dioxane-5-carboxylic acid ester of formula

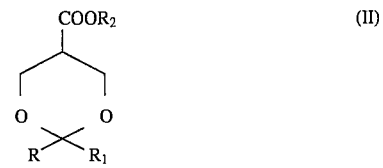

(II)

wherein $R_2$ represents a straight or branched $C_1$–$C_3$ alkyl group, a phenyl optionally substituted by nitro groups or a benzyl; into the corresponding amide of formula

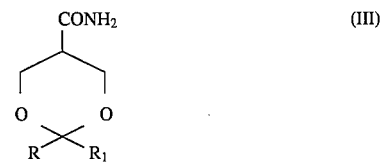

(III)

wherein R and $R_1$, have the above reported meanings and the subsequent rearrangement of the amide to obtain 5-amino-2,2-dialkyl-1,3-dioxanes of formula (I).

The compounds of formula (I) thus obtained can be used as such, for instance as described above and in the aforementioned British patent No. 1,472,050 to produce Iopamidol, or hydrolyzed according to conventional techniques to obtain serinol, which may then be used to produce Iopamidol. Specific examples of the compounds of formula (I) are:
5-amino-2,2-dimethyl-1,3-dioxane
5-amino-2,2-diethyl-1,3-dioxane
5-amino-2,2-di-n.propyl-1,3-dioxane
5-amino-2-ethyl-2-methyl-1,3-dioxane
3-amino-1,5-dioxaspiro[5.5]undecane
3-amino-1,5-dioxaspiro[4.5]decane Transformation of the ester of formula II into the corresponding amide of formula III may be carried out by treatment with ammonia, preferably in an aqueous solution. The compounds of formula III are then easily isolated by evaporating the solvent.

Rearrangement of the intermediate amides of formula III may be carried out by treatment with a hypohalogenite such as, for instance, sodium hypobromite or sodium hypochlorite, in an aqueous solution.

It is preferred to use sodium hypobromite, which may be prepared in situ from sodium hydroxide and bromine.

The ester compounds of formula II are known or easily prepared according to known methods (H. A. Bates et al., J. Org. Chem., 1986, 51. 2637–2641).

The 5-aminocarbonyl-2,2-dialkyl-1,3-dioxanes of formula III are new and they are a further object of the present invention.

Preparation of the amides, in general, can be carried out according to several standard methods described in the literature (see for a general review March, Advanced organic Chemistry, IV ed., pages 1275–1276). In this connection, without exceeding the scope of the present invention, 5-aminocarbonyl-2,2-dialkyl-1,3-dioxanes of formula III, can be thus prepared according to the aforementioned methods.

A preferred embodiment of the process of the present invention is the following.

A 2,2-dimethyl-1,3-dioxane-5-carboxylic acid ester is treated with an aqueous solution of ammonia for a few hours at room temperature. By evaporating the solvent the crude 5-aminocarbonyl-2,2-dimethyl-1,3-dioxane is obtained in practical quantitative yields and used as such in the subsequent rearrangement reaction.

5-Aminocarbonyl-2,2-dimethyl-1,3-dioxane is added to a basic aqueous solution of sodium hypobromite, prepared in situ from sodium hydroxide and bromine, and heated for a few hours at 80° C. After the evaporation of the water, the residue is collected and purified by treatment with an organic solvent affording 5-amino-2,2-dimethyl-1,3-dioxane in good yields.

5-Amino-2,2-dimethyl-1,3-dioxane is condensed with L-5-(2-acetoxy-propionylamino)-2,4,6-triido-isophthalic acid dichloride to obtain L-5-(2-acetoxy-propionylamino)-2,4,6-triido-isophthalic acid bis-(2,2-dimethyl-1,3-dioxane-5-yl-amide).

The latter can be rendered pure by re-crystallization from isopropanol. The ketal groups may be split by treatment with as little as 0.1N hydrochloric acid whereupon the substance dissolves. The pH of the solution is then adjusted to 11 whereupon the acetoxy group is saponified.

The process objects of the present invention are particularly suitable for an industrial application also because they use starting products which are easily prepared.

Both the intermediates and the starting products are stable and therefore do not present the risk of dangerous and unwanted reactions (explosions) during the accomplishment of the process.

Moreover the process objects of the present invention do not require drastic reaction conditions, such as for instance reduction at high pressures. Another particularly advantageous aspect is that the whole process is carried out in an aqueous environment allowing an easy recovery of the desired products in good yields.

With the aim to better illustrate the present invention, without limiting it, the following examples are now given.

EXAMPLE 1

Preparation of 5-aminocarbonyl-2,2-dimethyl-1,3-dioxane

A mixture of 2,2-dimethyl-5-ethoxycarbonyl-1,3-dioxane (4.1 g; 21.8 moles) and aqueous ammonia at 30% (10 ml) was kept under vigorous stirring for 20 hours.

At the end of the reaction the water was evaporated at reduced pressure; 3.4 g of crude 5-aminocarbonyl-2,2-dimethyl-1,3-dioxane (98% yield) were obtained, which could be used as such in the subsequent rearrangement reaction.

By crystallization from toluene 2.76 g of pure product (80% yield) were obtained.

$^1$H-NMR (DMSO-d,), δ (ppm), J (Hz): 1.27 (3H, s); 1.35 (3H, s); 2.6 (1H, m); 3.85 (4H, m); 7.0 (1H, bs); 7.3 (1H, bs).

$^{13}$C-NMR (DMSO-d$_6$), δ (ppm): 19.9 (q); 27.7 (q); 40.6 (d); 60.8 (t); 97.1 (s); 172.11 (s).

IR (KBr): cm$^{-1}$ 3360, 3200, 1665, 1635 Mass (m/e): 160 (M+1)$^+$

EXAMPLE 2

Preparation of 5-amino-2,2-dimethyl-1,3-dioxane

Bromine (6 g; 37.5 mmoles) was added dropwise in 5 minutes while keeping the temperature between 0° C. and 5° C., to a solution of sodium hydroxide (4.5 g; 112.5 mmoles) in water (22 ml) cooled at 0° C.

The mixture was kept under stirring at 0° C. for 15 minutes and 5-aminocarbonyl-2,2-dimethyl-1,3-dioxane (3 g; 18.75 mmoles) was added in one portion.

The mixture was kept under stirring at 0° C. for 1 hour; then it was heated at 80° C. for 16 hours.

At the end, water was evaporated under vacuum, the residue was collected with methylene chloride (25 ml), anhydrous sodium sulphate was added and stirring was maintained for 15 minutes.

The inorganic salts were removed by filtration and the solvent was evaporated at reduced pressure.

1.4 g of crude 5-amino-2,2-dimethyl-1,3-dioxane containing 5% of the starting material were obtained.

The pure product was obtained by distillation.

Preparation of 5-amino-2,2-dimethyl-1,3-dioxane

A mixture of 2,2-dimethyl-5-methoxycarbonyl-1,3-dioxane and 2,2-dimethyl-5-ethoxycarbonyl-1,3-dioxane having a GC titre of 77% and 18%, respectively (850 g; 3.76 moles and 0.814 moles, respectively) and aqueous ammonia at 30% (940 ml) was kept under vigorous stirring at room temperature and under nitrogen atmosphere for 24 hours.

At the end, the reaction mixture was cooled at 0° C. and kept under stirring for 60 minutes.

A solid was obtained which was filtered, washed with water (100 ml) and dried under vacuum at 70° C. affording 5-aminocarbonyl-2,2-dimethyl-1,3-dioxane (541 g; 74%. yield) which was used as such in the subsequent rearrangement reaction.

m.p. 132–134° C.

Preparation of 5-amino-2,2-dimethyl-1,3-dioxane

Bromine (6 g; 37.5 mmoles) was added dropwise in 5 minutes and keeping the temperature between 0° C. and 5° C., to a solution of sodium hydroxide (4.5 g; 112.5 mmoles) in water (22 ml) cooled at 0°C.

The mixture was kept under stirring at 0° C. for 15 minutes; the solution was added to 5-aminocarbonyl-2,2-dimethyl-1,3-dioxane (3 g; 18.75 mmoles).

It was kept under stirring at 0° C. for 1 hour; then it was heated at 0° C. for 16 hours.

At the end, water was evaporated under vacuum, the residue was collected with methylene chloride (25 ml), anhydrous sodium sulphate was added and stirring was maintained for 15 minutes.

The inorganic salts were removed by filtration and the solvent was evaporated at reduced pressure.

1.4 g of crude 5-amino-2,2-dimethyl-1,3-dioxane containing 5% of the starting material were obtained.

The pure product was obtained by distillation.

Preparation of 5-amino-2,2-dimethyl-1,3-dioxane

A solution of sodium hydroxide at 30% in water (122 ml) and a commercial solution of sodium hypochlorite 1.85 M (250 ml) were charged into a 600 ml reactor provided with mechanical stirrer, at 15° C. and under nitrogen atmosphere.

5-Aminocarbonyl-2,2-dimethyl-1,3-dioxane (60 g; 0.38 moles), prepared as described in example 3, was therein added and the suspension was kept at 15° C. under stirring for one hour.

The reaction mixture was gradually heated up to 70° C. in a period of 2 hours and kept under stirring at this temperature for 90 minutes.

At the end, the reaction mixture was distilled and 438 g of aqueous solution which, by titration with HCl0.1N resulted to contain 5-amino-2,2-dimethyl-1,3-dioxane (10.37% titre; 0.346 moles; 91.2% yield), were collected.

Such a solution was used as such in the following step.

HCl at 37% (33 ml) was added portionwise, in 30 minutes and at 25° C., to the aqueous solution prepared as above described (A).

The reaction mixture was kept under stirring at 40° C. for 60 minutes.

By evaporating the mixture under vacuum an oily residue, which was kept under stirring at 40° C., was obtained.

The crude product was crystallized from acetone (100 ml) and the solid obtained was filtered and washed with acetone (10 ml).

After drying under vacuum at 40° C., 34.5 g of 2-amino-1,3-propanediol hydrochloride (74% yield; GC titre 99%) were thus obtained. The serinol hydrochloride is converted into the corresponding free base by conventional techniques such as, for instance, by using ammonia or alkaline solutions.

Iopamidol may be formed by conventional techniques using either the serinol base material or its ketal, both as prepared herein. In general, either the serinol or its ketal prepared as in Examples 5 and 6, respectively, may be further reacted with 5-amino-2,4,6-triido-isophthalic acid dichloride or with its corresponding (2-acetoxy-propionyl) amino derivative, i.e., L-5-(2-acetoxy-propionylamino)-2,4, 6-triiodo-isophthalic acid dichloride. As is known in the industry when 5-amino-2,4,6-triiodo-isophthalic acid dichloride is used, a subsequent reaction with 2-acetoxypropionic acid is needed in order to functionalize the 5-amino group in the aromatic moiety.

Of course, a final deprotection step of the obtained products is required to obtain formation of the 5-(2-hydroxy-1-oxopyropyl) amino residue from the corresponding acetoxy derivative and to hydroloyze the ketal derivative. As explained in the aforementioned British patent GB 1,472, 050, the acyl group may be split off by hydrolysis in an alkaline medium and the ketal groups may be split off by hydrolysis in an acid medium.

What is claimed as new and is desired to be secured by Letters Patent of the United States is:

1. A process for the preparation of a 5-amino-2,2-dialkyl-1,3-dioxane of formula

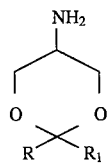

(I)

wherein R and $R_1$ are the same or different, and represent a straight or branched $C_1$–$C_3$ alkyl group or, together with the carbon atom to which they are bonded, form a $C_5$–$C_6$ cycloaliphatic ring; comprising transforming a 2,2-dialkyl-1,3-dioxane-5-carboxylic acid ester of formula

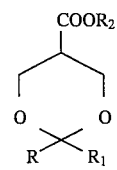

(II)

wherein $R_2$ represents a straight or branched $C_1$–$C_3$ alkyl group, a phenyl optionally substituted by nitro groups or a benzyl; into the corresponding amide of the formula

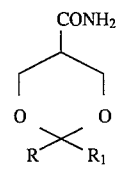

(III)

wherein R and $R_1$ have the above reported meanings and then subsequently rearranging said amide to obtain a 5-amino-2,2-dialkyl-1,3-dioxane of formula (I).

2. A process according to claim 1 wherein the transformation of the ester of formula II into the corresponding amide of formula III is carried out by treatment with ammonia in an aqueous solution.

3. A process according to claim 1 wherein the rearrangement of the amide is carried out by treatment with a hypohalogenite in an aqueous solution.

4. A process according to claim 3 wherein the hypohalogenite is sodium hypobromite.

5. A process according to claim 1 wherein the compound prepared is 5-amino-2,2-dimethyl-1,3-dioxane.

6. A compound of the formula

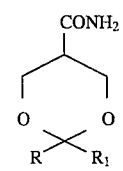

(III)

wherein R and $R_1$ are the same or different, and represent a straight or branched $C_1$–$C_3$ alkyl or, together with the carbon atom to which they are bonded, form a $C_5$–$C_6$ cycloaliphatic ring.

7. 5-Aminocarbonyl-2,2-dimethyl-1,3-dioxane.

8. A process for the preparation of a 5-amino-2,2-dialkyl-1,3-dioxane of formula

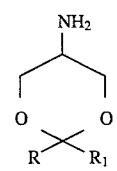

(I)

wherein R and $R_1$ are the same or different, and represent a straight or branched $C_1$–$C_3$ alkyl or, together with the carbon atom to which they are bonded, form a $C_5$–$C_6$ cycloaliphatic ring; comprising rearranging an amide of formula

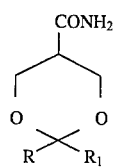 (III)

wherein R and R₁ have the above reported meanings, by treatment with a hypoalogenite in an aqueous solution to obtain a 5-amino-2,2-dialkyl-1,3-dioxane of formula (I).

9. A process for the preparation of Iopamidol from a 5-amino-2,2-dialkyl-1,3-dioxane of formula

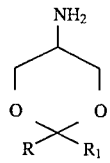 (I)

wherein R and R₁ are the same or different, and represent a straight or branched $C_1$–$C_3$ alkyl or, together with the carbon atom to which they are bonded, form a $C_5$–$C_6$ cycloaliphatic ring; comprising transforming a 2,2-dialkyl-1,3-dioxane-5-carboxylic acid ester of formula

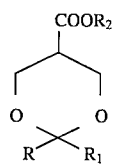 (II)

wherein $R_2$ represents a straight or branched $C_1$–$C_3$ alkyl group, a phenyl optionally substituted by nitro groups or a benzyl; into the corresponding amide of the formula

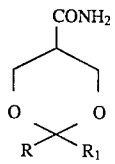 (III)

wherein R and R₁ have the above reported meanings; subsequently rearranging the aminocarbonyl compound to obtain a 5-amino-2,2-dialkyl-1,3-dioxane of the formula (I); reacting the dioxane or the hydrolysis product thereof with either (i) L-5-(2-acetoxy-propionylamido)-2,4,6-triido-isophthalic acid dichloride, or (ii) 5-amino-2,4,6-triido isophthalic acid dichloride followed by reaction of the resulting product of (ii) with 2-acetoxy-propionic acid chloride.

10. A process according to claim 9, wherein the transformation of the ester of formula II into the corresponding amide of formula III is carried out by treatment with ammonia in an aqueous solution.

11. A process according to claim 10, wherein the rearrangement is carried out by treatment with a hypohalogenite in an aqueous solution.

12. A process according to claim 9, wherein the dioxane is 5-amino-2,2-dimethyl-1,3-dioxane.

13. A process for the preparation of Iopamidol comprising; preparing a 5-amino-2,2-dialkyl-1,3-dioxane in the manner set forth in claim 1, adding hydrochloric acid to a solution of said dioxane to form 2-amino-1,3-propanediol hydrochloride; converting said hydrochloride into 2-amino-1,3-propanediol; and reacting said 2-amino-1,3-propanediol with L-5-(2-acetoxy-propionylamino)-2,4,6-triido-isophthalic acid dichloride.

14. A process for the preparation of 2-amino-1,3-propanediol or a salt thereof comprising; transforming a 2,2-dialkyl-1,3-dioxane-5-carboxylic acid ester of the formula

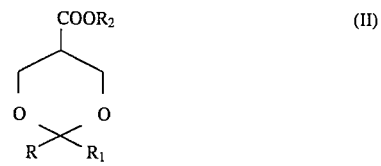 (II)

wherein R and R₁ are the same or different, and represent a straight or branched $C_1$–$C_3$ alkyl, or together with the carbon atom to which they are bonded, form a $C_1$–$C_3$ cycloaliphatic ring; $R_2$ represents a straight or branched $C_1$–$C_3$ alkyl group, a phenyl optionally substituted by nitro groups or a benzyl, into the corresponding amide of the formula

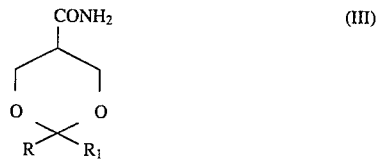 (III)

wherein R and R₁ have the above reported meanings; subsequently rearranging said amide to obtain a 5-amino-2,2-dialkyl-1,3-dioxane of the formula

 (I)

wherein R and R₁ have the above reported meanings; and subsequently hydrolysing said dioxane to obtain 2-amino-1,3-propanediol.

* * * * *

UNITED STATES PATENT AND TRADEMARK OFFICE
CERTIFICATE OF CORRECTION

Page 1 of 3

PATENT NO. : 5,580,993
DATED : December 3, 1996
INVENTOR(S) : MARCO VILLA ET AL.

It is certified that error appears in the above-identified patent and that said Letters Patent is hereby corrected as shown below:

On the title page, item [57], line 2 after Formula (I), "branched $C_1$ and $C_2$ alkyl" should read --branched $C_1$-$C_3$ alkyl--.

Column 1, line 14, "-bis(2-hydroxy-" should read -- -bis-[2-hydroxy- --;
line 15, "-2,4,6-triido-" should read -- -2,4,6-triiodo- --.
line 25, "-2,4,6-triido-" should read -- -2,4,6-triiodo- --.
line 45, "etheate" should read --etherate--.

Column 2, line 6, "1-5-(2 acetoxy" should read --L-5-(2-acetoxy--.
line 6, "-2,4,6-triido-" should read -- -2,4,6-triiodo- --.

Column 3, line 17, "-2,4,6-triido-" should read -- -2,4,6-triiodo- --.
line 19, "-2,4,6-triido-" should read -- -2,4,6-triiodo- --.
line 26, "process objects" should read --processes object--.
line 33, "process objects" should read -- processes object--.
line 47, "21.8 moles" should read --21.8 mmoles--.

Column 4, line 17, insert "EXAMPLE 3";
line 18, "5-amino -2,2-dimethyl-"should read --5 aminocarbonyl-2,2-dimethyl- --;
line 35, insert "EXAMPLE 4";
line 46, "heated at 0°C" should read --heated at 80°C--;

UNITED STATES PATENT AND TRADEMARK OFFICE
CERTIFICATE OF CORRECTION

PATENT NO. : 5,580,993
DATED : December 3, 1996
INVENTOR(S) : MARCO VILLA ET AL.

It is certified that error appears in the above-identified patent and that said Letters Patent is hereby corrected as shown below:

Column 4,  line 57, insert "EXAMPLE 5";
line 58, "5 amino-2,2-dimethyl-1,3-dioxane" should read --2-amino-1,3-propanediol hydrochloride--.

Column 5,  line 10, "HCl" at 37%" should read --B) HCl at 37%--.
line 32, "Examples 5 and 6" should read --Examples 5 and 4--;
line 33, "-2,4,6-triido-" should read -- -2,4,6-triodo- --;
line 45, "hydroloyze" should read --hydrolyze--.

Column 7,  lines 48 and 49, "propionylamido" should read --propionylamino--;
line 49, "-2,4,6-triido-" should read -- -2,4,6-triodo- --;
line 50, "-2,4,6-triido-" should read -- -2,4,6-triodo- --.

UNITED STATES PATENT AND TRADEMARK OFFICE
CERTIFICATE OF CORRECTION

PATENT NO. : 5,580,993
DATED : December 3, 1996
INVENTOR(S) : MARCO VILLA ET AL.

It is certified that error appears in the above-identified patent and that said Letters Patent is hereby corrected as shown below:

Column 8, line 3, "claim 10" should read --claim 9--;
line 13, "-2,4,6-triido-" should read -- -2,4,6-triiodo- --.
line 28, "form a $C_1$-$C_3$" should read --form a $C_5$-$C_6$--.

Signed and Sealed this

Twenty-third Day of February, 1999

Attest:

Q. TODD DICKINSON

*Attesting Officer*  *Acting Commissioner of Patents and Trademarks*